United States Patent [19]

Maruyama et al.

[11] Patent Number: 5,512,092
[45] Date of Patent: Apr. 30, 1996

[54] METHOD FOR PREPARING AQUEOUS EMULSION FOR COATING SOLID PHARMACEUTICAL PREPARATIONS

[75] Inventors: Naosuke Maruyama; Hiroyasu Kokubo; Shin-Ichiro Nakamura, all of Niigata, Japan

[73] Assignee: Shin-Etsu Chemical Co., Ltd., Tokyo, Japan

[21] Appl. No.: 420,569

[22] Filed: Apr. 12, 1995

[30] Foreign Application Priority Data

Apr. 15, 1994 [JP] Japan .................. 6-076913
Nov. 15, 1994 [JP] Japan .................. 6-280158

[51] Int. Cl.$^6$ .................................................. C09D 7/14
[52] U.S. Cl. ........................ 106/198; 106/187; 106/189; 106/203
[58] Field of Search ........................ 106/187, 189, 106/198, 203

[56] References Cited

U.S. PATENT DOCUMENTS

| | | | |
|---|---|---|---|
| 3,556,826 | 1/1971 | Gronholz et al. | 106/170 |
| 4,330,338 | 5/1982 | Banker | 106/170 |
| 4,385,078 | 5/1983 | Onda et al. | 106/170 |
| 4,814,015 | 3/1989 | Quinaln | 106/170 |
| 4,968,350 | 11/1990 | Bindschaedler et al. | 106/170 |

*Primary Examiner*—David Brunsman
*Attorney, Agent, or Firm*—Sughrue, Mion, Zinn, Macpeak & Seas

[57] ABSTRACT a method for preparing an aqueous emulsion for coating solid pharmaceutical preparations comprises the steps of dissolving a cellulosic polymer in a mixed solvent of water and an organic solvent capable of being admixed with water in any rate to give a polymer solution, self-emulsifying the polymer solution by mixing with water and then concentrating the resulting emulsified stock solution. The concentration is carried out by removing a part of the liquid components while passing it through a membrane for ultrafiltration till the polymer concentration of the resulting emulsion reaches a level of not less than 7% by weight.

10 Claims, No Drawings

METHOD FOR PREPARING AQUEOUS EMULSION FOR COATING SOLID PHARMACEUTICAL PREPARATIONS

BACKGROUND OF THE INVENTION

The present invention relates to a method for preparing an aqueous emulsion for coating solid pharmaceutical preparations.

Solid pharmaceutical preparations have been coated with a variety of coating bases depending on the applications thereof. In an enteric coated pharmaceutical preparation, the enteric coating serves to not only protect a drug having low resistance to acids from the attack thereof in the stomach, but also protect the gastric mucous membrane from the attack of the drug which may stimulate and damage the wall of the stomach and is dissolved after the arrival at the intestines wherein the pharmaceutical preparation shows its desired pharmacological action. In addition, a sustained release pharmaceutical preparation provided with an insoluble coating ensures the control of the release properties of a drug and continuously shows its pharmacological effect over a long time period. There have been used cellulosic polymers as enteric coating bases. Examples of water-insoluble cellulosic polymers usable as enteric coating bases include cellulose acetate phthalate, hydroxypropylmethyl cellulose phthalate, hydroxypropylmethyl cellulose acetate succinate and carboxymethylethyl cellulose. Moreover, bases for sustained release coating films may, for instance, be ethyl cellulose. These polymers as coating bases are used in the coating treatment of pharmaceutical preparations in the form of a solution in an organic solvent or an aqueous latex or an aqueous dispersion. Recently, however, the use of organic solvents has been regulated from the viewpoint of environmental pollution and accordingly, coating treatments which makes use of aqueous systems have widely been adopted.

There have been known methods for dispersing cellulosic polymers in water, for instance, a method comprising adding the polymers to water together with salts or neutralizing the carboxyl groups of the polymers and a method comprising dispersing, in water, the polymers which are pulverized into fine particles in advance.

With regard to the former method, Japanese Patent Application Publication No. 61-56221 discloses a method which comprises the steps of emulsifying cellulose acetate phthalate, then adding a phosphoric acid salt as an anticoagulant and spray-drying the resulting emulsion to give polymer powder capable of being redispersed in water. In this method, the emulsification of ethyl cellulose and cellulose acetate phthalate is carried out according to the method as disclosed in U.S. Pat. No. 4,177,177. Moreover, Japanese Patent Provisional Publication No. 56-30913 discloses a method in which cellulose acetate phthalate or hydroxypropylmethyl cellulose phthalate is used in coating operations in the form of an aqueous solution neutralized with ammonia. Furthermore, Japanese Patent Provisional Publication No. 58-135807 discloses a method comprising the steps of dissolving a cellulose derivative in water after neutralization with an alkali and then adding a carboxylic acid. In all of the solid pharmaceutical preparations prepared according to these methods, alkali or ammonium salts of carboxylic acids remain in the coated films of the preparations. The alkali and ammonium salts are highly hygroscopic by nature and accordingly, the quality of such solid pharmaceutical preparations is impaired.

In respect of the latter method, Japanese Patent Application Publication No. 56-12614 discloses a method comprising dispersing a cellulosic polymer having an average particle size of not more than 100 μm in water which comprises a gelling agent (a plasticizer) and has a boiling point of not less than 100° C. Moreover, Japanese Patent Application Publication Nos. 57-53329 and 58-55125 disclose the use of triacetin or triethyl citrate as a gelling agent. If a polymer is mechanically pulverized to disperse it in water, the particle size of the resulting polymer particles is more than 1 μm. The use of a plasticizer is indispensable to the dispersion, in water, of polymer particles having a particle size of more than 1 μm and, otherwise, these polymer particles are softened through heating and cause coagulation and precipitation within the resulting dispersions.

Japanese Patent Application Publication No. 3-39490 discloses a method for improving the technique for coating an aqueous cellulose system by reducing the particle size of a cellulosic polymer dispersed in water through emulsification. In this patent, the emulsification is carried out according to the method as disclosed in U.S. Pat. No. 4,177,177. More specifically, a polymer solution is first prepared by dissolving the cellulosic polymer in a water-immiscible organic solvent. Thereafter a hydrocarbon (such as cetyl alcohol) having not less than 8 carbon atoms as a stabilizer and a surfactant are added to the polymer solution and then the resulting polymer solution is treated with a special emulsifying device such as a high-pressure homogenizer to give an emulsion. As has been discussed above in detail, the conventional aqueous coating solutions include components other than the cellulosic polymers, such as stabilizers and surfactants. These components often impair the resistance to acids and stability of the resulting enteric coated pharmaceutical preparations. For this reason, there has been desired for the development of a coating solution having a simple composition as much as possible.

SUMMARY OF THE INVENTION

The present invention has been developed for the solution of the foregoing problems associated with the conventional methods and accordingly, it is an object of the present invention to provide a method for preparing a stable aqueous emulsion for coating solid pharmaceutical preparations, which can easily be emulsified without addition of any additive such as emulsifying agents, polymerization initiators, chain transfer agents, salts and/or plasticizers.

The foregoing object of the present invention can effectively be accomplished by providing a method for preparing an aqueous emulsion for coating solid pharmaceutical preparations which comprises the steps of dissolving a cellulosic polymer in a mixed solvent of water and an organic solvent capable of being admixed with water in any rate to give a polymer solution and then self-emulsifying the polymer solution through addition of water to thus give an emulsified stock solution which is subsequently concentrated.

DETAILED EXPLANATION OF THE INVENTION

The cellulosic polymers used in the preparation method of the present invention serve as base materials for coating solid pharmaceutical preparations. Examples of such cellulosic polymers serving as enteric bases include hydroxypropylmethyl cellulose phthalate, hydroxypropylmethyl cellulose acetate succinate, cellulose acetate phthalate, cellulose acetate trimellitate and carboxymethylethyl cellulose. In addition, examples of sustained release bases include ethyl cellulose. These cellulosic polymers may be used alone or in any combination.

Examples of the organic solvents which can be admixed with water in any rate include alcohols such as methanol, ethanol and isopropanol; and ketones such as acetone and methyl ethyl ketone. These organic solvents may likewise be used alone or in any combination. In this respect, a water-immiscible solvent may, if necessary, be used in a small amount.

The mixed solvent of water and such an organic solvent must have a composition which can ensure the dissolution of the cellulosic polymer. The rate of water in the mixed solvent may vary depending on the kinds of the cellulosic polymers to be dissolved in the solvent, but is in general not more than 60% by weight.

The polymer solution preferably has a concentration of not more than 10% by weight and more preferably between 2 and 10% by weight. This is because if the concentration exceeds 10% by weight, the viscosity of the resulting solution is extremely high, gel-like substances are separated out of the solution and accordingly, the polymer cannot be dispersed into an emulsion having a particle size of less than 1 µm, while if it is less than 2% by weight, the aqueous emulsion finally prepared has a low concentration and this results in a low productivity rate.

The amount of water to be mixed with the polymer solution is preferably not less than 80% by weight and more preferably 80 to 300% by weight on the basis of the weight of the polymer solution. If the amount of water is less than 80% by weight, the emulsification of the polymer solution is incomplete due to insufficient dispersion of the solvent. On the other hand, it exceeds 300% by weight, the aqueous emulsion finally prepared has an extremely low concentration and this results in a low productivity rate. Moreover, the weight ratio of the organic solvent to water is preferably not more than 2:8. In other words, water is preferably added in an amount beyond the foregoing ratio. If the weight ratio exceeds the ratio 2:8 or the amount of water is less than the ratio, any stable emulsion cannot be prepared and the polymer solution often causes precipitation during treating the same. A surfactant may be added to the emulsified stock solution during the concentration process of the stock solution.

The emulsification process is carried out by dissolving a cellulosic polymer in a mixed solvent of the foregoing organic solvent and water to give a polymer solution and then mixing the polymer solution with water in a predetermined ratio to complete the emulsification. The mixture is gently and continuously stirred during the emulsification process using a stirring machine currently used. In this respect, the emulsification is not affected by the strength of the stirring operation at all. The mixing of the polymer solution and water may be performed by introducing a desired amount of water into an organic phase or conversely by introducing an organic phase into a desired amount of water. In this respect, however, if a water phase is introduced into an organic phase and the stirring speed is low, the organic solvent in the polymer solution does not sufficiently diffuse into the water phase and thus an emulsion having a particle size of not more than 1 µm cannot be obtained. The resulting emulsified stock solution has a low concentration and contains organic solvents. Accordingly, the solution cannot be used without any post-treatment. More specifically, the stock solution must be concentrated prior to use as a coating solution.

The concentration is performed by removing a part of the liquid components through a membrane for ultrafiltration so as to adjust the polymer concentration to a level of not less than 7% by weight. If the polymer concentration is less than 7% by weight, the coating of solid pharmaceutical preparations requires a long time period and thus the productivity rate is impaired. The membrane for ultrafiltration is a porous film having a molecular cutoff of 50,000 or 200,000. Examples of materials for such porous films are polysulfone, polyvinylidene fluoride, cellulose acetate and ceramics. In addition, examples of ultrafiltration modules include flat films and tubular, spiral and hollow fibers. Heating is not needed in the concentration performed through the use of ultrafiltration modules and the ester bonds at the carboxylic acid groups of the cellulosic polymer are not cleaved through heating. Therefore, any free acid is not generated during the concentration procedure and the resulting polymer is completely dissolved at a predetermined pH value. Moreover, the time required for the concentration is shorter than that required for the concentration by heating.

The coating treatment is performed by spraying solid pharmaceutical preparations with a coating solution using a coating device and simultaneously drying the sprayed solution to form a coating film. The coating solution used herein is obtained by adding a pharmaceutically acceptable plasticizer such as triethyl citrate or triacetin to the aqueous emulsion thus prepared. Examples of coating device usable herein include fluidized-bed coaters, pan coaters and air-vented rotary drum type coaters.

According to the method of the present invention for concentrating an aqueous emulsion for coating solid pharmaceutical preparations, a cellulosic polymer can easily be dispersed into an emulsion by once dissolving the polymer in an organic solvent having a particular composition without addition of any additives such as a salt and/or an emulsifying agent (surfactant). Moreover, an emulsified stock solution is concentrated through a membrane for ultrafiltration in the method of the invention. Therefore, an aqueous emulsion having a high concentration for coating can be prepared within a short time period without using any heating process. Thus, enteric pharmaceutical preparations having excellent resistance to acids and stability can be prepared by coating solid pharmaceutical preparations with the aqueous emulsion.

Examples of the present invention will hereunder be described in detail, but the present invention is not restricted to these specific Examples and these specific Examples can properly be modified.

EXAMPLE 1

Hydroxypropylmethyl cellulose phthalate (HP-55 available from Shin-Etsu Chemical Co., Ltd.; 1.06 kg) was dissolved in 25.74 kg of a 7:3 (weight ratio) ethanol/water mixed solvent to give a polymer solution. To the resulting polymer solution, there was added 153.36 kg of water at a rate of 10 kg/sec while stirring the solution at a strength of 100 rpm to give an emulsion. The resulting emulsified stock solution was concentrated, at room temperature, to a solid content of 15% by weight by passing it through a flat membrane of polysulfone having a molecular cutoff of 200,000 and a filtration area of 0.65 $m^2$. The rate of inhibition of the membrane against the hydroxypropylmethyl cellulose phthalate was found to be 100%.

The emulsion having a solid content of 15% by weight was diluted with four volumes of water and again concentrated to a solid content of 15% by weight in the same manner used above. The average permeate flow during the concentration was found to be 60 l/m²·hr. The amount of the ethanol remaining in the concentrate was determined by gas chromatography and found to be 2.1% by weight and the content of free acids present therein was found to be 0.32% by weight.

Furthermore, the concentrate obtained through the foregoing process was diluted with 9 volumes of water to a solid content of 15% by weight. The average permeate flow during the concentration was found to be 55 l/m²·hr. The amount of the ethanol remaining in the concentrate was determined by gas chromatography and found to be 0.19% by weight and the content of the free acids present therein was found to be 0.33% by weight.

An aqueous emulsion having a concentration of 15% by weight was obtained in a yield of 6.4 kg after the foregoing operations. The average particle size of the resulting emulsion was found to be 0.2 μm.

EXAMPLE 2

Hydroxypropylmethyl cellulose acetate succinate (Shin-Etsu AQOAT AS-MG available from Shin-Etsu Chemical Co., Ltd.; 531 g) was dissolved in 12.8 kg of an 8:2 (weight ratio) ethanol/water mixed solvent to give a polymer solution. To the resulting polymer solution, there was added 76.7 kg of water at a rate of 5 kg/sec while stirring the solution at 100 rpm to give an emulsion. The resulting emulsified stock solution was concentrated, at room temperature, to a concentration of 10% by weight by passing it through a flat membrane of polysulfone having a molecular cutoff of 200,000 and a filtration area of 0.65 m². The rate of inhibition of the membrane against the hydroxypropylmethyl cellulose acetate succinate was found to be 100% and the average permeate flow during the concentration was found to be 55 E/m²·hr.

EXAMPLE 3

Ethyl cellulose (N-7-G available from Shin-Etsu Chemical Co., Ltd.; 0.05 kg) was dissolved in 4.95 kg of ethanol to give a polymer solution. To the resulting polymer solution, there was added 20 kg of water at a rate of 5 kg/sec while stirring the solution at 100 rpm to give an emulsion. The resulting emulsified stock solution was concentrated, at room temperature, to a concentration of 10% by weight by passing it through a flat membrane of polysulfone having a molecular cutoff of 200,000 and a filtration area of 0.83 m². The rate of inhibition of the membrane against the ethyl cellulose was found to be 100% and the average permeate flow during the concentration was found to be 50 l/m²·hr.

COMPARATIVE EXAMPLE 1

Hydroxypropylmethyl cellulose phthalate (HP-55 available from Shin-Etsu Chemical Co., Ltd.; 600 g) was dissolved in 29.1 kg of a 8:2 (weight ratio) ethanol/water mixed solvent to give a polymer solution. To the resulting polymer solution, there was added 30 kg of water at a rate of 8 kg/sec while stirring the solution at 100 rpm to give an emulsion. The weight ratio of the organic solvent to water in the resulting emulsified stock solution was found to be 39:60. The stock solution was concentrated, at room temperature, to a concentration of 10% by weight by passing it through a flat membrane of polysulfone having a molecular cutoff of 200,000 and a filtration area of 0.65 m², but hydroxypropylmethyl cellulose phthalate was precipitated during the concentration and this made the concentration impossible.

COMPARATIVE EXAMPLE 2

Hydroxypropylmethyl cellulose phthalate (HP-55 available from Shin-Etsu Chemical Co., Ltd.; 50 g) was dissolved in 950 g of acetone to give a polymer solution. To the resulting polymer solution, there was added 1 kg of water at a rate of 200 g/sec while stirring the solution at 100 rpm to give an emulsion. The emulsified stock solution thus obtained was concentrated by subjecting it to vacuum distillation, according to the usual manner, at a jacket temperature of 50° C. and a degree of vacuum of −400 mmHg to remove the solvents and then removing water while raising the jacket temperature to 80° C.

The distillate was passed through a 200 mesh sieve to remove flocculates. The content of the flocculates was found to be 10.3% by weight and the polymer concentration was found to be 10% by weight. The average particle size of the polymer dispersed in the emulsion thus prepared was 0.4 μm. The resulting emulsion comprised 1.05% by weight of free acids which was higher than the free acid concentration, i.e., 0.31% by weight, observed prior to the concentration.

What is claimed is:

1. A method for preparing an aqueous emulsion for coating solid pharmaceutical preparations comprising the following steps (a) to (c):

(a) dissolving a water-insoluble cellulosic polymer in an organic solvent capable of being admixed with water in any rate or a mixed solvent of the organic solvent and water to give a polymer solution having a polymer concentration of not more than 10% by weight;

(b) self-emulsifying the polymer solution by addition of water in an amount of not less than 80% by weight of the polymer solution to give an emulsified stock solution; and (c) removing a part of the solvents present in the emulsified stock solution to concentrate it.

2. The method for preparing an aqueous emulsion as set forth in claim 1 wherein, in the foregoing step (c), the emulsified stock solution is concentrated to a polymer concentration of not less than 7% by weight through ultrafiltration.

3. The method for preparing an aqueous emulsion as set forth in claim 1 wherein the cellulosic polymer is at least one member selected from the group consisting of hydroxypropylmethyl cellulose phthalate, hydroxypropylmethyl cellulose acetate succinate, cellulose acetate phthalate, cellulose acetate trimellitate, carboxymethylethyl cellulose and ethyl cellulose.

4. The method for preparing an aqueous emulsion as set forth in claim 1 wherein the organic solvent is at least one member selected from the group consisting of methanol, ethanol, isopropanol, acetone and methyl ethyl ketone.

5. The method for preparing an aqueous emulsion as set forth in claim 1 whereto the content of the water in the mixed solvent is not more than 60% by weight.

6. A method for preparing an aqueous emulsion for coating solid pharmaceutical preparations comprising the following steps (a) to (c):

(a) dissolving a water-insoluble cellulosic polymer in a mixed solvent comprising an organic solvent capable of being admixed with water in any rate and a water-immiscible solvent to give a polymer solution having a polymer concentration of not more than 10% by weight;

(b) self-emulsifying the polymer solution by addition of water in an amount of not less than 80% by weight of the polymer solution to give an emulsified stock solution: and (c) removing a part of the solvents present in the emulsified stock solution to concentrate it.

7. The method for preparing an aqueous emulsion as set forth in claim 6 wherein the content of the water in the mixed solvent is not more than 60% by weight.

8. The method for preparing an aqueous emulsion as set forth in claim 6 wherein, in the foregoing step (c), the emulsified stock solution is concentrated to a polymer concentration of not less than 7% by weight through ultrafiltration.

9. The method for preparing an aqueous emulsion as set forth in claim 6 wherein the cellulosic polymer is at least one member selected from the group consisting of hydroxypropylmethyl cellulose phthalate, hydroxypropylmethyl cellulose acetate succinate, cellulose acetate phthalate, cellulose acetate trimellitate, carboxymethylethyl cellulose and ethyl cellulose.

10. The method for preparing an aqueous emulsion as set forth in claim 6 wherein the organic solvent is at least one member selected from the group consisting of methanol, ethanol, isopropanol, acetone and methyl ethyl ketone.

\* \* \* \* \*